United States Patent [19]

Pike et al.

[11] Patent Number: 5,340,585

[45] Date of Patent: * Aug. 23, 1994

[54] METHOD AND FORMULATIONS FOR USE IN TREATING BENIGN GYNECOLOGICAL DISORDERS

[75] Inventors: Malcolm C. Pike, Long Beach; Darcy V. Spicer, Pasadena, both of Calif.

[73] Assignee: University of Southern California, Los Angeles, Calif.

[*] Notice: The portion of the term of this patent subsequent to May 18, 2010 has been disclaimed.

[21] Appl. No.: 62,883

[22] Filed: May 17, 1993

Related U.S. Application Data

[63] Continuation-in-part of Ser. No. 952,513, Dec. 3, 1992, which is a continuation-in-part of Ser. No. 684,612, Apr. 12, 1991, Pat. No. 5,211,952.

[51] Int. Cl.$^5$ .......................... A61F 2/02; A61F 6/06; A61K 37/38; A61K 9/50

[52] U.S. Cl. .................................. 424/426; 423/423; 423/432; 423/443; 423/451; 423/489; 423/490; 423/496; 423/497; 423/DIG. 14

[58] Field of Search ............... 424/426, 422, 423, 424, 424/432, 433, 443, 484, 485, 486, 487, 488, 489, 490, 496, 497, DIG. 14; 514/843, 2, 12, 21, 800, 841, 842; 530/313, 850, 853; 128/830, 832, 833

[56] References Cited

U.S. PATENT DOCUMENTS

| | | | |
|---|---|---|---|
| 3,731,683 | 5/1973 | Zaffaroni | 424/434 |
| 3,797,494 | 3/1974 | Zaffaroni | 424/434 |
| 4,264,575 | 4/1981 | Zimmerman et al. | 424/432 |
| 4,336,243 | 6/1982 | Sanvordeker et al. | 424/449 |
| 4,762,717 | 8/1988 | Crowley, Jr. | 424/425 |
| 5,211,952 | 5/1993 | Spicer et al. | 424/426 |

OTHER PUBLICATIONS

Watts et al, "Effects of Oral Estrogens and Esterified Estrogens & Androgen on Bone Mineral Density in Post Menopause Women", *The 2nd Annual Meeting North American Menopause Society Program*, S-F16, Sep. 25-28, 1991.

Bergkvist et al., "The Risk of Breast Cancer After Estrogen and Estrogen–Progestin Replacement", *N.E.J. of Med.*, 321:5, pp. 293–297 (Aug. 3, 1989).

Burger et al., "The Management of Persistent Menopausal Symptoms with Oestradiol–Testosterone Implants: Clinical, Lipid and Hormonal Results", *Maturitas*, 6: 351–358 (1984).

Chetkowski et al., "Biologic Effects of Transdermal Estradiol", *N.E. J. of Med.*, 314: 5, pp. 1615–1620 (Jun. 19, 1986).

Conn et al., "Gonadotropin–Releasing Hormone and its Analogues", *N.E. J. of Med.*, 324: 2, pp. 93–103 (Jan. 10, 1991).

Cowsar et al., "Biodegradable and Nonbiodegradable Fibrous Delivery Systems", *Long Acting Contraceptive Delivery Systems* pp. 145–162 (eds. Zatuchni et al. 1984).

Diczfalusy et al., "Some Pharmacokinetic and Pharmacodynamic Properties of Vaginal Delivery Systems That Release Small Amounts of Progestogens at a Near Zero-Order Rate", *Long-Acting Contraceptive Delivery Systems*, pp. 213–227 (eds. Zatuchni et al. 1984).

Donnez et al., "Treatment of Uterine Fibroids with Implants of Gonadotropin–releasing Hormone Agonist: Assessment by Hysterography", *Fertility and Sterility*, 51: 6,, pp. 947–950 (Jun. 1989).

Farish et al., "The Effects of Hormone Implants on Serum Lipoproteins and Steroid Hormones in Bilaterally Oophorectomised Women", *Act Endocrinologica*, 106:116–120 (1984).

(List continued on next page.)

Primary Examiner—Thurman K. Page
Assistant Examiner—Carlos Azpuru
Attorney, Agent, or Firm—Robbins, Berliner & Carson

[57] ABSTRACT

Compositions and methods which are effective to treat benign gynecological disorders for extended periods of time in women in who the risk of endometrial stimulation is minimized or absent are described, wherein an effective amount of a gonadotropin hormone releasing hormone composition and an effective amount of an estrogenic composition are provided over a period of time, optionally with addition of an androgenic composition.

21 Claims, No Drawings

OTHER PUBLICATIONS

Ferguson et al., "Compudose: An Implant System for Growth Promoting and Feed Efficiency in Cattle", *J. of Controlled Release*, 8;45–54 (1988).

George et al., *Int. J. Fertil.*, 34: 19–24 (1989).

Garza-Flores et al., "Development of a Low-Dose Monthly Injectable Contraceptive *Contraception 30:*" 79 (1984).

Gennant et al., "Quantitative Computed Tomography of Vertebral Spongiosa: A Sensitive Method for Detecting Early Bone Loss After Oophorectomy", *Annals of Internal Medicine*, 97: 5, pp. 699–705 (Nov. 1982).

Gilley et al., "Development of Controlled-Release Progesterone Microcapsules for the Regulation of Fertility During Lactation", *Southern Research Inst.* 73–74.

Kaufman, M. et al., *J. Clin. Oncol.*, y: 1113–19 (1989).

Hahn, et al., "Development of Microencapsulated Norgestimate as a Long-Acting Contraceptive", *Long-Acting Contraceptive Delivery Systems*, pp. 97–112 (eds. Zatuchni et al., 1984).

Hsieh et al., "Subcutaneous Controlled Administration of Estradiol From Compudose Implants: In Vitro and In Vivo Evaluations", *Rutgers University*, pp. 134–135.

Hsieh et al., "Enhanced Release of Drugs From Silicone Elastomers (I) Release Kinetics of Pineal and Steroidal Hormones", *RVG Development and Industrial Pharmacy*, 11(6&7) 1391–1410 (1985).

Jackanicz, Theordone M., "Vaginal Ring Steroid-Releasing Systems", *Long-Acting Contraceptive Delivery Systems*, pp. 200–211 (eds Zatuchni et al., 1984).

Lewis et al., "Polymeric Considerations in the Design of Microencapsulation of Contraceptive Steroids", *Long-Acting Contraceptive Delivery Systems*, pp. 76≧95 (eds. Zatuchni et al., 1984).

Lewis, Danny H., "Controlled Release of Bioactive Agents from Lactide/Glycolide Polymers", *Stolle Research and Development Corporation*, pp. 1–43.

Mertola et al., "Successful Treatment of Severe Premenstrual Syndrome by Combined Use of Gonadotropin-Releasing Hormone Agonist and Estrogen/Progestin", *J. of Clin. Endocrinology and Metabolism*, pp. 252A–252F (1991).

Lobo et al., "Subdermal Estradiol Pellets Following Hysterectomy and Oophorectomy", *Amer. Journal of Obstetrics & Gyn.* 138: 714–719 (1980).

Nezhat et al., "Estradiol Implants for Conception Control", *Amer. Journal of Obstetrics & Gyn.* 138: 1151–1156 (1980).

Notelovitz et al., "Influence of Extended Treatment With Oral Estrogens/Androgen Combination on Lipids and Lipoproteins in Surgically Menopausal Women", *North American Menopause Society*, 1991 Meeting Abstract, S-B5 (Montreal Canada 1991).

Nuwayser et al., "Microencapsulation of Contraceptive Steroids", *Long-Acting Contraceptive Delivery Systems*, pp. 65–75 (eds. Zatuchni et al. 1984).

Pike et al., "LHRH Agonists and the Prevention of Breast and Ovarian Cancer", *Br. J. Cancer*, 60: 142–148 (1989).

Pitt et al., "Capronor-A Biodegradable Delivery System for Levonorgestrel", *Long-Acting Contraceptive Delivery Systems*, pp. 48–63 (eds. Zatuchni et al. 1984).

Ralston et al., "Effect of Subdermal Oestrogen and Oestrogen/Testosterone Implant on Calcium and Phosphorus Homeostasis After Oophorectomy", *Maturitas*,, 6: 341–344 (1984).

Roy et al., "Vaginal Ring Clinical Studies: Update", *Long-Acting Contraceptive Delivery Systems*, pp. 581–594 (eds. Zatuchni et al. 1984).

Sandow et al., "Clinical Pharmacokinetics of LHRH Analogues", *LHRH Analogues in Gynaecology*, pp. 17–31.

Sherwin et al., "Postmenopausal Estrogen and Androgen Replacement and Lipoprotein Lipid Concentrations", *Am. J. Obstet. Gynecol.*, 156: 414–419 (1987).

Stanczyk et al., "A Randomized Comparison of Nonoral Estradiol Delivery in Postmenopausal Women", *Am. J. Obstet. Gynecol.* 159: 6, pp. 1540–1546 (Dec. 1988).

Urman et al., "Elevated Serum Testosterone, Hirsutism, and Virilism Assoicated With Combined Androgen-Estrogen Hormone Replacement Therapy", *Obstetrics & Gynecology* 77: 4, , pp. 595–598 (Apr. 1991).

Zorn et al., "Treatment of Endometriosis with a Delayed Release Preparation of the Agonist D-Trp$^6$-luteinizing Hormone-releasing Hormone: Long-term Follow-up in a Series of 50 Patients", *Fertiity & Sterility*, 53: 3, pp. 401–406 (Mar. 1990).

Youngs et al., "Effects on an Oral Estrogen-Androgen Preparation on Lipoprotein Lipids in Postmenopausal Women: a Pilot Study", *North American Menopause Society 1991 Meeting Abstract*, P. 130 (Montreal Canada 1991).

METHOD AND FORMULATIONS FOR USE IN TREATING BENIGN GYNECOLOGICAL DISORDERS

This application is a continuation-in-part of Ser. No. 07/952,513 filed Dec. 3, 1992, which in turn is a continuation-in-part of Ser. No. 07/684,612 filed Apr. 12, 1991, now U.S. Pat. No. 6,211,952.

BACKGROUND OF THE INVENTION

This invention relates to methods for treating benign gynecological disorders, reducing the risk of cancers of the breast and ovary, decreasing density on mammograms and decreasing breast parenchyma, as well as to formulations for use in such methods. More particularly, the present invention is directed to methods and preparations effective in treating benign gynecological disorders, including premenstrual syndrome, for extended periods of time. Pursuant to the method of the invention, ovarian hormone production is suppressed and only estrogens (and, optionally, androgens) are replaced in order to treat benign gynecological disorders; ovarian progesterone is not replaced. The formulations are for use in women in whom the risk of endometrial stimulation is minimized or absent. Such women include those who have had a prior hysterectomy, those who are using a progesterone releasing intrauterine device, and those who receive other progestogens from their physicians.

Gonadotropin releasing hormone (GnRH), also known as luteinizing hormone releasing hormone (LHRH), produced by the hypothalamus controls the secretion of follicle stimulating hormone (FSH) and luteinizing hormone (LH) by the pituitary and thence gonadal steroid hormone production. Potent synthetic agonists of GnRH administered to premenopausal women have been shown to produce a transient rise in FSH/LH release followed by a sustained suppression.

Inhibition of ovulation by GnRH agonists has been found, as expected, to be dose-related. When administered in a dose just high enough to ensure anovulation, the ovaries may continue to produce estrogen. This is an unstable situation, with different women having widely varying serum estrogen levels. There has also been concern that endometrial hyperplasia would occur in some women, while in others there would be periods of hypoestrogenemia with unacceptable vasomotor symptoms and probably loss of bone mineral content. "High-dose" GnRH agonists have been observed to uniformly reduce serum estradiol and serum progesterone to oophorectomized levels. The development of "high dose" depot formulations of GnRH agonists permits sustained inhibition of ovulation and suppression of ovarian steroid production, as well as improved ease of drug administration. The treatment is reversible; in a study of 50 patients, recovery of menstrual function occurred on average at 87 days (range 44–126 days following 6–8 months treatment with the GnRH agonist tryptorelin [Zorn, J. -R. et al., Fertil.Steril. 53:401–06 (1990)]. Other depot formulations of GnRH agonists produce similar sex-steroid suppresion including decapeptyl [George, M. et al., Int.J.Fertil. 34:19–24 (1989)], goserelin [Kaufman, M. et al., J.Clin.Oncol. 7:1113–19 (1989)] and buserline [Donnez, J. et at., Fertil.Steril. 51:947–50 (1989)].

In spite of their clear effectiveness, side effects attendant to the use of "high-dose" GnRH agonists have prevented their general adoption. Common side effects reported to occur with depot GnRH agonists in premenopausal patients include: hot flashes, vaginal dryness, irregular vaginal bleeding and fatigue. Additional side effects that have been reported in some patients receiving GnRH agonists include: sweating, headache, depression, lability in mood, nausea and/or vomiting, nervousness, insomnia, pollakisuria, weight gain, sleepiness, dizziness, decreased libido and mild breast tenderness or swelling.

A recent review article reflects current thinking about GnRH and its analogues [Conn, P. M. and Crowley, Jr., W. F., "Gonadotropin-Releasing Hormone and Its Analogues, "N.Engl.J.Med. 324:93–103 (1991)]. The The authors note at pages 96–97 that "whether to supplement GnRH-agonist analogues with sex steroids is a complex decision"; they propose estrogen replacement followed by the administration of a progestational agent "at physiologic doses and in a physiologic (i.e., sequential) pattern."

U.S. Pat.No. 4,762,717 to Crowley, Jr., the entire disclosure of which is hereby incorporated by reference, is based on the above-noted assumption that administration of a progestational agent should be effected in a sequential pattern so as to mimic the phases of the menstrual cycle. The patent describes contraceptive methods for female animals using luteinizing hormone releasing hormone (LHRH) compositions in combination with sex steroids. The patent calls for administering LHRH (or analogs, agonists or antagonists thereof) in a first delivery system combined with continuous administration of an effective amount of estrogenic steroids during the "follicular phase" of the menstrual cycle beginning at the onset of "normal menses". A second delivery system is administered during the "luteal phase" of the menstrual cycle until the onset of "normal menses". The second delivery system comprises the LHRH/estrogenic steroid combination and additionally provides an effective dosage of a progestational steroid.

This administration sequence is designed to mimic the physiological secretion of steroids in the menstrual cycle. As a consequence, each delivery system is effective for a period of only about two weeks (corresponding to the typical length of each of the follicular and luteal phases, according to the designation of Crowley).

The approach of Crowley is clearly unacceptable when considered in light of current knowledge about the long-term effects of administering the components thereof for the periods of time specified. The proposed level of estrogen administration (i.e., to achieve an estradiol concentration of about 50 to about 140 pg/ml for a human female) in the two delivery system approach of Crowley is unnecessarily high and the proposed amount of progestogen to be administered unnecessarily high. Epidemiologic case-control studies of postmenopausal breast cancer risk and estrogen replacement therapy (ERT) using population controls suggest that increased exposure to exogenous estrogen leads to an increased risk of breast cancer in a dose-dependent fashion. Moreover, administration of progestational steroid for about two weeks of every approximately 28-day treatment cycle was associated with unacceptable risks to the patient in a recent epidemiological study of breast cancer [Bergkvist, L. et al., N.Engl.J.Med. 321:293-97 (1989)]: the study suggests that the addition of progestogen during the latter half of the 28-day ERT cycle may double the risk associated with use of estrogen alone.

Pike, M. C. et al., *Br. J. Cancer* 60:142–48 (1989), the entire disclosure of which is also hereby incorporated by reference, have proposed a contraceptive regimen in which "high-dose" LHRH agonist treatment is coupled with estrogen replacement therapy (ERT), specifically 0.625 mg of conjugated equine estrogens for 21 days in each 28-day treatment cycle. The administration of a progestational steroid is proposed to be limited to a 10–16 day interval every three or four cycles. It is now clear that the 7-day period in each treatment cycle when ERT is not provided would be associated in many patients with symptoms of estrogen withdrawal, such as hot flushes. Moreover, a negative calcium balance could develop during the period of hypoestrogenemia with the possibility of resultant osteoporosis. Finally, blood cholesterol levels would likely be adversely affected during that time. Therefore, it is unlikely that the specific regimen proposed by Pike et al. would be found acceptable.

Administration of various compositions comprising sex hormones has also been contemplated in connection with the treatment of various benign gynecological disorders, such as endometriosis, fibroids and polycystic ovarian syndrome. One particularly prevalent disorder for which hormonal therapy has been contemplated is late luteal phase dysphoric disorder (commonly referred to as premenstrual syndrome). The essential feature of late luteal phase dysphoric disorder is a pattern of clinically significant emotional and behavioral symptoms that occur during the last week of the luteal phase and remit within a few days after the onset of the follicular phase. In most females, these symptoms occur in the week before and remit within a few days after the onset of menses. Non-menstruating females who have had a hysterectomy but retain ovarian function may also report similar symptoms. Among the most commonly experienced symptoms are the following: marked affective lability (e.g., sudden episodes of sadness or irritability); persistent feelings of irritability, anger or tension; feelings of depression and self-deprecating thoughts; decreased interest in usual activities; fatigue and loss of energy; a subjective sense of difficulty in concentrating; changes in appetite; cravings for specific foods; sleep disturbance; breast tenderness or swelling; headaches; joint or muscle pain; a sensation of bloating; and weight gain. The symptoms are often so severe as to seriously interfere with work or with usual social activities or relationships with others.

It has been reported that administration of a GnRH agonist may ameliorate some of the symptoms of premenstrual syndrome [Mortola, J. F. et al., *J. Clin. Endocrin. & Metab.* 72:252A–252F (1991)]. In addition to administration of GnRH agonist alone, the study included in a 28-day regimen combinations of GnRH agonist with conjugated equine estrogen (CEE) on days 1–25, with medroxyprogesterone acetate (MPA) on days 16–25, and with both CEE on days 1–25 and MPA on days 16–25. The authors concluded that the use of 0.625 mg CEE on days 1–25 and 10 mg MPA on days 16–25 would provide a safe and effective method of obtaining the beneficial effects of GnRH agonist on premenstrual syndrome. Unfortunately, this type of regimen (calling for addition of progestogen during the latter half of each 28-day ERT cycle) for treatment of premenstrual syndrome would be subject to the same objections previously noted for comparable contraceptive regimens, i.e., a possible doubling of the breast cancer risk associated with use of estrogen alone (Bergkvist et al., supra).

Androgens have been administered in these settings to improve sexual functioning, but there are significant negative effects. The administration of even a low dose (e.g., 1.25 to 2.5 mg) of an oral androgen, such as methyltestosterone, with oral estrogens is associated with detrimental changes in blood cholesterol patterns [Notelovitz, M. et al., "Influence of extended treatment with oral estrogens/androgen combination on lipids and lipoproteins in surgically menopausal women," *North American Menopause Society*, 1991, Meeting Abstract S-B5 (Montreal, Canada 1991); Youngs, D. D. & Sherwin, B. B., "Effects of an oral estrogen-androgen preparation on lipoprotein lipids in postmenopausal women: a pilot study," *North American Menopause Society*, 1991, Meeting Abstract P-130 (Montreal, Canada 1991). The addition of testosterone implants to estrogen appears to have only a small impact on cholesterol patterns. While it may negate the positive beneficial effects of the estrogen on cholesterol, a detrimental effect is not clearly seen [Farish, E. et al., "The effects of hormone implants on serum lipoproteins and steroid hormones in bilaterally oophorectomized women," *Acta Endocrinologica* 106: 116–20 (1984)].

The use of pellets of testosterone unfortunately results in large variations in serum levels of testosterone over time. High levels are observed shortly after administration [Burger, H. G. et al., "The management of persistent menopausal symptoms with estradiol-testosterone implants: clinical, lipid and hormonal results," *Maturitas* 6: 351–8 (1984)]. Elevated serum testosterone levels with associated virilization or masculinization can occur with repeated administration, if caution is not used [Urman, B. et al., "Elevated serum testosterone, hirsutism, and virilism associated with combined androgen-estrogen hormone replacement therapy, "*Obstet. Gynecol.* 77: 595–8 (1991)]. Further, the serum testosterone levels achieved with such approaches may be substantially above usual levels is normal premenopausal women [Sherwin, B. B. et al., "Postmenopausal estrogen and androgen replacement and lipoprotein lipid concentrations," *Am. J. Obstet. Gynecol.* 156: 414–9 (1987)].

It is an object of the present invention to provide a regimen which would obviate a number of problems attendant to existing treatments of various benign gynecological disorders in women in whom the risk of endometrial stimulation is minimized or absent, while at the same time reducing the risk of adverse consequences associated with the heretofore known methods.

SUMMARY OF THE INVENTION

In accordance with the present invention, there are provided compositions and methods for treating benign gynecological disorders in a human female in whom the risk of endometrial stimulation by estrogenic compositions is minimized or absent, wherein a GnRH composition, an estrogenic composition, and optionally an androgenic composition are administered according to specific protocols as defined herein. In all of these protocols, over a period of time (on the order of about 1 month to several years or longer), a GnRH composition is administered in an amount effective to suppress ovarian estrogen and progesterone production, inhibiting ovulation. Over this period of time, in all protocols an amount of an estrogenic composition effective to prevent symptoms and signs of estrogen deficiency is also administered; the symptoms and signs of estrogen deficiency which may develop during prolonged therapy with a GnRH composition include, but not are not limited to, symptoms of the menopause, vasomotor instability, harmful alterations in serum cholesterol or its fractions, and urogenital atrophy. Optionally, an androgenic composition is administered over the period of time in conjunction with the administration of the GnRH composition and estrogenic composition as previously described. The androgenic composition is administered in an amount effective to restore a patient's effective androgen level to a normal premenopausal level, and in particular to maintain bone mineral density.

Use of delivery systems for long-term release of GnRH agonists, requiring infrequent administration, makes the inventive regimens both practical and potentially more effective in treating various benign gynecological disorders. Moreover, in accordance with the present invention the levels of estrogen replacement would be significantly lower than those proposed as suitable in human female patients by Crowley. Further, the administration of progestational compositions would not occur. Among the advantages is reducing exposure to progestogens is a reduction in the risk of a number of complications associated with progestogen exposure. For example, progestogens are key breast mitogens and may lead to increased breast cancer risk. In addition, progestogens have been associated with late luteal phase dysphoria disorder and with uterine fibroids.

The regimens of the present invention are effective in treating several benign gynecological disorders, including but not limited to late luteal phase dysphoric disorder (premenstrual syndrome), fibroids, endometriosis and polycystic ovarian syndrome. In addition, the use of a long-term administration depot provides greater convenience of administration. The reduction in the amount of compositions administered also has the effect of reducing the projected rate of incidence of breast cancer, as well as reducing the incidence of various benign gynecological disorders. The invention further reduces the risk of ovarian cancer, as is known to occur with combination-type oral contraceptive use.

DETAILED DESCRIPTION OF THE INVENTION

Pursuant to the present invention, the regimen of the present invention comprises a slow-release (or depot) formulation which is effective for an extended period of time. This extended period of time is substantially longer than is the case with either delivery system of Crowley, each of which is designed to be replaced after only a two-week period. Typically, the depot formulation of the invention is effective over an extended period of time of at least about one month. Depending on the composition and mode of administration, the inventive formulation may be effective for six months or more; formulations effective for from one up to five or more years are contemplated as within the scope of the present invention. It is presently preferred that the formulation be effective over about a three or four month period.

A number of compounds have been developed to inhibit effective release or action of gonadotropin releasing hormone (GnRH), including both agonists and antagonists of GnRH. While the following detailed disclosure describes in particular the use of GnRH agonists, other GnRH analogues (such as GnRH antagonists) and GnRH itself may also be employed in a manner known per se for essentially complete suppression of LH and FSH in formulations in accordance with the invention, and are hereinafter referred to as "GnRH compositions." The GnRH compositions provide continuous suppression of pituitary gonadotropin secretion, thereby inhibiting ovulation.

A GnRH agonist formulation, leuprolide acetate depot (LAD), is commercially available in the United States and lasts about 4 weeks. A 16-week formulation of buserelin has been tested [Donnez, J. et al., *Fertil. Steril.* 51:947–950 (1989)]. Longer acting formulations of leuprolide acetate or other gonadotropin compositions are also contemplated as within the scope of the invention. Other suitable GnRH compositions which may be administered in a suitable time-release formulation are described in the aforementioned U.S. Pat. No. 4,762,717 and the patents cited therein. These include decapeptyl, buserelin, nafarelin, deslorelin, histrelin, gonadorelin and [(Imbzl)-D-His$^6$-Pro$^9$-Net]GnRH.

The dose of GnRH composition must be sufficient to completely suppress ovarian estrogen production, so that estrogen effects are predictably related to the administered estrogen. The amount of GnRH composition effective to achieve the desired suppression of ovarian estrogen production may readily be determined with respect to any given GnRH composition and for any given mammal. In the combined administration of an effective dose of GnRH composition, the dose range depends upon the particular GnRH composition used, but is in an amount effective to suppress LH and FSH. The effective dose ranges, as well as being compound specific, may also depend upon patient characteristics, such as age and weight. Further, the effective amount of GnRH composition also depends upon route of administration. Thus, administration by subcutaneous or intramuscular routes typically requires less GnRH composition than administration by transdermal or vaginal routes. An effective dose range of GnRH composition is thus determined by routine testing by one of skill in the art without undue experimentation. The GnRH composition may comprise a single active agent or a combination of two or more such agents. In general, it is expedient to administer the active GnRH composition in an amount between about 0.0001 and 10 mg/kg of body weight per day. It is understood in the art that this range may vary depending upon whether a GnRH antagonistic analogue or a GnRH agonistic analogue, or combination of the two, is administered.

GnRH compositions are in general absorbed very well across a wide variety of surfaces. Thus, subcutaneous, intramuscular, vaginal and transdermal routes of administration have all proven to be effective, and would be suitable for use in accordance with the present invention. In an embodiment of this invention, administration of the delivery system is made via the intramuscular route. Thus, the GnRH composition is administered via an intramuscular delivery system using an excipient which effects a slow degradation of the delivery system.

Many of the side effects of GnRH composition use reflect the hypoestrogenic state induced and can thus be prevented in accordance with the present invention by add-back estrogen therapy. Accordingly, a second component of a regimen in accordance with the present invention is an effective amount of an estrogenic composition to prevent symptoms and signs of estrogen deficiency, e.g., prevent symptoms and signs of the menopause, including adverse alterations in serum cholesterol.

As the add-back estrogen, a single-component natural or synthetic estrogen composition or a combination of such compositions can be used to maintain a constant systemic level. A substantial body of information exists concerning the effects of hormone replacement therapy after a natural or surgical menopause. Although more is known about the effects of conjugated equine estrogens (CEE) as estrogen replacement therapy (ERT) than any other agent, it is presently preferred that a single-component or two-component composition be employed.

As used herein, estrogenic compositions refer to both the natural and the synthetic materials. These materials are well known in the art. Natural and synthetic estrogenic compositions which can be used according to the invention described herein include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol and estrone potassium sulfate. Equine estrogens, such as equilelinin, equilelinin sulfate and estetrol, may also be employed.

Typical dose ranges for estrogenic compositions depend not only upon the choice of composition, but also upon the characteristics of the patient. For an adult human female patient administered estradiol, typical dose ranges are such that the serum level of estradiol is maintained at a level of about 25 to about 140 pg/ml. Most preferably, the serum level of estradiol is about 30 to about 50 pg/ml, which is significantly lower than the preferred serum level of 80 to 120 pg/ml called for by Crowley.

In accordance with the present invention, the effective dosage of an estrogenic composition is preferably delivered in the same delivery system as the GnRH composition, although the excipient composition and/or formulation may differ. The delivery system thus allows complete suppression of gonadotropins, removal of reproductive function of the ovaries, and complete suppression of ovarian steroidogenesis for the extended period of time for which the system is designed to be effective; at the same time, there is a replacement of sufficient levels of estrogen to minimize or eliminate the long-term side effects of GnRH composition administration.

In accordance with another embodiment of the present invention, an androgenic composition is administered in conjunction with administration of GnRH composition and estrogenic composition as previously described. The androgenic composition is administered in an amount to increase a patient's effective androgen level to a level not exceeding the normal premenopausal level, and in particular in concert with the estrogenic composition to maintain bone mineral density. Administration to oophorectomized women of the androgen, methyltestosterone, has been shown to add significantly to the bone preserving action of ERT; women on the combined regimen actually increased their bone mass [Watts, N. et al., "Effects of oral esterified estrogens and esterified estrogens plus androgens on bone mineral density in postmenopausal women," *North American Menopause Society*, Meeting Abstract, (Montreal, Canada 1991)] Restoration of a patient's normal androgen levels is desirable, as administration of other components of the formulations in accordance with the invention has the effect of reducing serum androgen levels, in some case significantly. For purposes of the present invention, normal androgen levels are on the order of about 20 to about 80 ng/dl for testosterone.

Suitable androgenic hormones for use in accordance with the present invention include but are not limited to testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone. Typical dose ranges for androgenic hormones depend upon the choice of composition and the individual patient. For an adult human female administered testosterone, typical doses are administered to provide serum levels of testosterone of from about 20 ng/dl to about 80 ng/dl, and preferably about 40 to about 60 ng/dl.

In accordance with the present invention, the delivery vehicle of the invention provides for administration of GnRH composition, estrogenic composition, and optionally androgen by a subcutaneous, intramuscular, vaginal or transdermal route. The carrier vehicle for each component is selected from a wide variety of materials which are already known per se or may hereafter be developed which provide for controlled release of the compositions in the particular physiological environment. In particular, the carrier vehicle of the delivery system is selected such that near zero-order release of the components of the regimen is achieved. In the context of the present invention, the carrier vehicle should therefore also be construed to embrace particular formulations of the compositions which are themselves suitable for providing near zero-order release. A targeted steady-state release can be obtained by suitable adjustment of the design or composition of the delivery system. Known devices suitable for use as a delivery system in accordance with the present invention include, for example, drug-delivery pump devices providing near zero-order release of the components of the regimen.

One suitable formulation to achieve the desired near zero-order release of the components comprises injectable microcapsules or microspheres prepared from a biodegradable polymer, such as poly(dl-lactide), poly(dl-lactide-co-glycolide), polycaprolactone, polyglycolide, polylactic acid-co-glycolide, poly(hydroxybutyric acid), a polyortho-ester or a polyacetal. Injectable systems comprising microcapsules or microspheres of a diameter on the order of about 50 to about 500 μm offer advantages over other delivery systems. For example, they generally use less hormone and may be administered by paramedical personnel. Moreover, such systems are inherently flexible in the design of the duration and rate of separate drug release by selection of microcapsule or microsphere size, drug loading and dosage administered. In addition, such microcapsules or microspheres can be successfully sterilized with gamma irradiation.

Microcapsules or microspheres are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery. The mechanism of release in biodegradable microcapsules is a combination of drug diffusion and polymer biodegradation. Therefore, the rate and duration of release are determined by microcapsule size, drug content and quality, and polymer parameters, such as crystallinity, molecular weight and composition. In particular, adjustment in the amount of drug released is generally achieved by modification of capsule wall thickness, capsule diameter, and/or polymer composition.

Detailed information concerning the design and use of microspheres and microcapsules is provided by, e.g., Lewis, D. H., "Controlled release of bioactive agents from lactide/glycolide polymers," in Chasin, M. & Langer, R. (eds.), *Biodegradable Polymers as Drug Delivery Systems*, pp. 1–41 (1990), the entire disclosure of which is hereby incorporated by reference. Several methods are currently available for preparing microcapsules or microspheres. As discussed in Nuwayser, E. S. et al., "Microencapsulation of contraceptive steroids," in Zatuchni, G. L. et al. (eds.), *Long-acting Contraceptive Delivery Systems*, pp. 64–76 (1984), the entire disclosure of which is hereby incorporated by reference, most of these methods can be classified under three major categories: coacervation, coagulation and air-suspension coating.

An exemplary material for use in the formulation of suitable microcapsules or microspheres is poly(dl-lactide-co-glycolide) as described in Lewis, D. H. & Tice, T. R., "Polymeric considerations in the design of microencapsulation of contraceptive steroids," in Zatuchni, G. L. et al. (eds.), *Long-acting Contraceptive Delivery Systems*, pp. 77–95 (1984), the entire disclosure of which is hereby incorporated by reference. The solvent evaporation process described therein is suitable for preparing microcapsules or microspheres in a size range acceptable for administration by conventional syringe and needle; moreover, the yield or fraction of microcapsules or microspheres within a desired size range can be selected and achieved with appropriate process adjustments. This enables the preparation of diffusional controlled-release formulations in which the duration of drug release is directly related to total surface area or particle size. Another exemplary material is poly(ε-caprolactone) as described in Pitt, C. G. & Schindler, A., "Capronor—A biodegradable delivery system for levonorgestrel," in Zatuchni, G. L. et al. (eds.), *Long-acting Contraceptive Delivery Systems*, pp. 48–63 (1984), the entire disclosure of which is hereby incorporated by reference. Other biodegradable polymeric materials suitable for preparation of microcapsules for controlled (i.e., near zero-order) release would be readily determined through routine experimentation by those skilled in the art.

An alternative delivery system suitable for use in accordance with the present invention comprises fibers or filaments comprising the active agents and biodegradable or non-biodegradable polymers. Precision delivery systems can be mass-produced by this method; moreover, geometrically configured controlled-release devices can be produced by, e.g., wrapping drug-releasing fibers around conventional intravaginal rings or other intravaginal devices. Typically, fibrous delivery systems rely on membrane-moderated diffusion mechanisms to control the rate and duration of drug release. Monolithic drug-releasing fibers may be prepared by conventional spinning processes; when reservoir-type fibrous systems are desired, either a fast-releasing monolithic fiber is prepared and then coated with a rate-controlling sheath, or a coaxial spinning process is employed, in which the drug is extruded as the core of the fiber at the same time as the rate-controlling polymer sheath. Suitable fibers for providing zero-order release of the active agents and methods for the preparation thereof are described in Cowsar, D. E. & Dunn, R. L., "Biodegradable and nonbiodegradable fibrous delivery systems," in Zatuchni, G. L. et al. (eds.), *Long-acting Contraceptive Delivery Systems*, pp. 145–163 (1984), the entire disclosure of which is hereby incorporated by reference.

Other suitable materials for preparation of such devices include silicon-based materials, such as polydimethylsiloxanes, which have been employed to prepare capsule-type, matrix-type and microsealed drug delivery systems. For example, a suitable device may be prepared by coating a non-medicated silicone rubber core with a thin layer of silicone rubber (such as MDX-4-4210 Clean Grade Elastomer, available from Dow Corning) which contains micronized crystalline forms of the active agents. An implant of this type (for administration of estradiol) is described in Ferguson, T. H. et al., "Compudose: an implant system for growth promotion and feed efficiency in cattle," *J. Controlled Release* 8, 45–54 (1988), the entire disclosure of which is hereby incorporated by reference. Improved matrix release devices may be prepared by incorporating water-soluble carriers, such as sodium alginate, or by using additives, such as co-solvents or salts, which enhance the release rate of active agents from the polymer matrix.

In general, contraceptive vaginal rings may be designed as homogeneous mixtures of composition and silastic; as a core vaginal ring surrounded by silastic; as a shell ring with a core of silastic, surrounded by a layer of composition and silastic covered by a tube of silastic; as a band ring of inert silastic with a drug-containing band on the ring; or as a combination of the various designs to permit the specific release characteristics desired. In this regard, useful systems are described in the following: Jackanicz, T. M., "Vaginal ring steroid-releasing systems," pp. 201–12; Diczfalusy, E. & Landgren, B.-M., "Some pharmacokinetic and pharmacodynamic properties of vaginal delivery systems that release small amounts of progestogens at a near zero-order rate," pp. 213–27; and Roy, S. & Mishell, Jr., D. R., "Vaginal ring clinical studies: update," pp. 581–94: all in Zatuchni, G. L. et al. (eds.), *Long-acting Contraceptive Delivery Systems* (1984), the entire disclosures of which are hereby incorporated by reference.

For transdermal delivery of the active agents, suitable pads or bandages are also well known in the art. Typically, these pads comprise a backing member defining one exterior surface, a surface of pressure-sensitive adhesive defining a second exterior surface, and disposed therebetween a reservoir containing the active agents confined therein. Suitable transdermal delivery systems are disclosed in U.S. Pat. Nos. 3,731,683 and 3,797,494 to Zaffaroni and U.S. Pat. No. 4,336,243 to Sanvordeker et al., the entire disclosures of which are hereby incorporated by reference.

Other suitable formulations would be readily apparent to those of skill in the art. For example, with certain active agents, administration may be effected subcutaneously or intramuscularly with slowly-dissolving pellets of crystalline or microcrystalline materials, or directly as a crystalline or microcrystalline aqueous suspension. The important features are maintenance of near zero-order release of the drugs over the desired treatment periods, followed by a relatively rapid decrease in serum concentrations to low levels once the relevant portion of the treatment regimen has been completed.

The inventive regimen is designed to reduce the degree of adverse effects associated with the use of GnRH compositions and estrogen in accordance with the heretofore known protocols, such as those of Crowley and Pike et al. For example, GnRH compositions have been recognized as having an adverse impact on bone metabolism. Bone mineral density (BMD) is known to fall after a natural or surgical menopause; the fall is most evident in regions of trabecular bone. A net loss of BMD has been seen in the majority of studies after 6 months of GnRH agonist treatment, well in excess of even the greatest rates of fall of approximately 1%/yr that have been reported in premenopausal women. This loss of BMD is secondary to the reduction in estrogens and androgens. In accordance with the present invention, ERT combined with optional androgen is administered to reduce BMD loss in postmenopausal women. The reduction in BMD loss is mirrored in a much reduced fracture risk in ERT treated postmenopausal women. Similarly, the ability of ERT to control hot flashes and other menopausal symptoms is also well documented. By combining GnRH composition therapy with appropriate levels of estrogen and, optionally, androgen replacement therapy the effects of the hypoestrogenic state induced by the GnRH composition are prevented. One effect of the optional use of androgens is to enable a reduction in the dose of estrogen necessary to prevent loss of BMD.

An increased risk of cardiovascular disease has been a further concern with the long-term use of a GnRH composition, as such an increase has been associated with oophorectomy at a young age. According to the present invention, add-back estrogen is employed to reduce the risk of cardiovascular disease. As is the case when ERT is given to postmenopausal women, one reason for this reduction in risk is likely to be the beneficial effects of estrogen on serum cholesterol. GnRH agonists may have effects on cholesterol which are not mediated by their effects on serum estrogens. The GnRH plus add-back estrogen is predicted to result in a beneficial rise in high density lipoprotein cholesterol or HDLC (increase from add-back estrogen) and no change in low density lipoprotein cholesterol or LDLC (increase from GnRH agonist balanced by comparable decrease from add-back estrogen), a clearly beneficial overall effect. The addition of optional androgen replacement may slightly increase LDLC and slightly decrease HDLC, but the overall predicted effect of the proposed regimen remains beneficial.

While estrogen thus has significant positive effects in conjunction with the use of a GnRH composition, it is nonetheless important to recognize the potential risks inherent in such treatment. For example, a substantial body of evidence has shown that ovarian hormones are critical factors in the etiology of breast cancer. Including a reversible "medical oophorectomy" through the use of a GnRH composition given at a dose sufficient to suppress ovarian function to postmenopausal levels in accordance with the present invention similarly achieves a major reduction in a woman's lifetime breast cancer risk. Add-back therapy with low-dose estrogen is, however, required to prevent harmful hypoestrogenic effects. Thus, the present invention strives for an appropriate balance in the combined effect of a GnRH composition and the add-back hormone regimen so as to minimize subsequent breast cancer risk.

If there were no increased breast cancer risk from ERT in the postmenopausal period, then the prototype GnRH composition plus add-back estrogen regimen should substantially reduce breast cancer risk as it should simply be equivalent to temporary bilateral oophorectomy. A more cautious approach is to assume that the addition of add-back estrogen to the GnRH composition regimen causes some increase in breast cancer risk when compared to the use of GnRH composition alone. The addition of the optional androgen would have no effect on breast cancer risk.

An estimate of the effect of a preferred four-month prototype (Example 1) on lifetime breast cancer risk is shown in Table 1. Table 1 shows that lifetime breast cancer risk is predicted to be reduced in accordance with the present invention by 31% if used for 5 years and by 53% if used for 10 years.

Finally, the present invention is designed to reduce the risk of ovarian cancer. Protective risk factors that have been consistently found in epidemiological studies of ovarian cancer are early menopause, high parity and use of combination-type oral contraceptives (COCs). With increasing parity or increasing duration of COC use ovarian cancer risk decreases steadily. The suppression of ovulation by GnRH compositions should protect against ovarian cancer to the same or greater extent than COCs. The addition of ERT and optionally androgen to the GnRH composition regimen should have no effect on this reduced risk.

Table 1 shows the predicted relative risks for ovarian cancer of using the prototype regimen for 5, 10 or 15 years at premenopausal ages. The calculations were based on using the regimen at any time during the premenopausal period. Use for 5 years is predicted to reduce the lifetime risk of ovarian cancer by as much as 41%; use for 10 years should reduce the risk by 67%.

TABLE 1

| Predicted Relative Reduction in Lifetime Risk of Cancer With Prototype Regimen (Example 1) | | | |
|---|---|---|---|
| Duration of Regiment (years) | 5 | 10 | 15 |
| Breast | 31% | 53% | 70% |
| Ovary | 41% | 67% | 84% |

The following examples will serve to illustrate the invention without in any way being limiting thereon.

EXAMPLE 1

This example describes a delivery system for intramuscular administratoon over a 4-month duration. The delivery system administers a GnRH composition (buserelin) and a natural estrogenic steroid (estradiol), such that the amount of GnRH composition is sufficient to suppress LH and FSH secretion during the entire period of administration, with the serum level of estradiol being maintained at about 40 pg/ml. The buserelin is provided at a dose of 6.6 mg, which is sufficient to maintain serum levels on the order of 30 pg/ml throughout the treatment cycle. The estradiol is provided in a dose of 5 mg. Both the buserelin and estradiol are provided in the form of microspheres prepared from a copolymer of lactide and glycolide; as is well known in the art, this copolymer provides for an effective time-release formulation which is biodegradable. Optionally, androgen is provided in a dose of 24 mg of testosterone. The serum level of testosterone is maintained at about 50 ng/dl. The testosterone is provided in the form of microspheres prepared from a copolymer of lactide and glycolide.

EXAMPLE 2

This example describes a vaginal ring. A shell ring of estradiol releases about 180 μg/day and thereby achieves serum levels of about 40 pg/ml for its 120 days of use. Buserelin is also released to achieve serum levels of about 30 pg/ml. The vaginal ring is replaced with a fresh ring about every 120 days.

While there have been shown and described the fundamental novel features of the invention, it will be understood that various omissions, substitutions and changes in the form and details of the regimens illustrated may be made by those skilled in the art without departing from the spirit of the invention. It is the intention, therefore, to be limited only as indicated by the scope of the following claims.

What is claimed is:

1. A composition comprising:
   a slow-release formulation of a gonadotropin hormone releasing hormone composition which maintains serum level of said gonadotropin hormone releasing hormone composition in a female mammal at a level effective to suppress ovarian estrogen and progesterone production over a period of time, wherein said gonadotropin hormone release hormone composition is administered at a rate between about 0.0001 and 10 mg/kg of body weight per day; and
   a slow-release formulation of an estrogenic composition which maintains serum level of said estrogenic composition over said period of time at a level effective to prevent symptoms and signs of estrogen deficiency, wherein said serum level of said estrogenic composition is equivalent to serum estrodiol levels in the range of about 25 to about 140 pg/ml.

2. A composition according to claim 1, wherein said gonadotropin hormone releasing hormone composition is selected from the group consisting of gonadotropin hormone releasing hormone, gonadotropin hormone releasing hormone analogues, gonadotropin hormone releasing hormone agonists, gonadotropin hormone releasing hormone antagonists and mixtures thereof.

3. A composition according to claim 2, wherein said gonadotropin hormone releasing hormone composition is a gonadotropin hormone releasing hormone agonist selected from the group consisting of leuprolide acetate, goserelin, decapeptyl, buserelin, nafarelin, deslorelin, histrelin, gonadorelin, [(Imbzl)-D-His$^6$-Pro$^9$-Net]GnRH and mixtures thereof.

4. A composition according to claim 1, wherein said estrogenic composition is selected from the group consisting of estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilelinin, equilelinin sulfate, estetrol and mixtures of two or more thereof.

5. A composition according to claim 1, wherein said period of time is about one month to about five years.

6. A composition according to claim 5, wherein said period of time is about three months to about four months.

7. A composition according to claim 1, for administration by a subcutaneous, intramuscular, vaginal or transdermal route.

8. A composition according to claim 1, further comprising:
   a slow-release formulation of an androgenic hormone which increases serum level of said androgenic hormone over said period of time to a level not exceeding normal premenopausal levels for a patient, wherein said serum level of said androgenic composition is equivalent to serum testosterone levels in the range of about 20 to about 80 ng/dl.

9. A composition according to claim 8, wherein said androgenic hormone is selected from the group consisting of testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone.

10. A method for treating benign gynecological disorders in a patient in whom risk of endometrial stimulation by estrogenic compositions is minimized or absent, comprising:
    administering a gonadotropin hormone releasing hormone composition for a first period of time in an amount effective to maintain serum level of said gonadotropin hormone releasing hormone composition at a level effective to suppress ovarian estrogen and progesterone production, wherein said gonadotropin hormone releasing hormone composition is administered at a rate between about 0.0001 and 10 mg/kg of body weight per day; and
    simultaneously administering an estrogenic composition in an amount effective to maintain serum level of said estrogenic composition over said first period of time at a level effective to prevent signs and symptoms of estrogen deficiency, wherein said serum level of said estrogenic composition is equivalent to serum estradiol levels in the range of about 25 to about 140 pg/ml.

11. A method according to claim 10, wherein said gonadotropin hormone releasing hormone composition is selected from the group consisting of gonadotropin hormone releasing hormone, gonadotropin hormone releasing hormone analogues, gonadotropin hormone releasing hormone agonists, gonadotropin hormone releasing hormone antagonists and mixtures thereof.

12. A method according to claim 11, wherein said gonadotropin hormone releasing hormone composition is a gonadotropin hormone releasing hormone agonist selected from the group consisting of leuprolide acetate, goserelin, decapeptyl, buserelin, nafarelin, deslorelin, histrelin, gonadorelin, [(Imbzl)-D-His$^6$-Pro$^9$-Net]GnRH and mixtures thereof.

13. A method according to claim 10, wherein said estrogenic composition is selected from the group consisting of estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilelinin, equilelinin sulfate, estetrol and mixtures of two or more thereof.

14. A method according to claim 10, further comprising administering an androgenic composition over said period of time in an amount effective to increase effective androgen level to a level not exceeding normal premenopausal levels for a patient, wherein said serum level of said androgenic composition is equivalent to serum testosterone levels in the range of about 20 to about 80 ng/dl.

15. A method according to claim 14, wherein said androgenic hormone is selected from the group consisting of testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone.

16. A method according to claim 10, wherein said period of time is about one month to about five years.

17. A method according to claim 16, wherein said period of time is about three months to about four months.

18. A composition according to claim 1, wherein said serum level of said estrogenic composition is equivalent to serum estradiol levels in the range of about 30 to about 50 pg/ml.

19. A composition according to claim 1, wherein said serum level of said androgenic composition is equivalent to serum testosterone levels in the range of about 40 to about 60 ng/dl.

20. A method according to claim 10, wherein said serum level of said estrogenic composition is equivalent to serum estradiol levels in the range of about 30 to about 50 pg/ml.

21. A method according to claim 10, wherein said serum level of said androgenic composition is equivalent to serum testosterone levels in the range of about 40 to about 60 ng/dl.

* * * * *

UNITED STATES PATENT AND TRADEMARK OFFICE
CERTIFICATE OF CORRECTION

PATENT NO. : 5,340,585
DATED : August 23, 1994
INVENTOR(S) : Malcolm C. Pike, et al.

It is certified that error appears in the above-indentified patent and that said Letters Patent is hereby corrected as shown below:

Column 2, line 14, delete "The".

Column 11, line 64, delete "Including" and insert --Inducing--

Column 12, line 57, delete "administratoon" and insert --administration--

Signed and Sealed this

First Day of November, 1994

Attest:

BRUCE LEHMAN

*Attesting Officer*          *Commissioner of Patents and Trademarks*